United States Patent

Alt

[11] Patent Number: 5,855,600
[45] Date of Patent: Jan. 5, 1999

[54] FLEXIBLE IMPLANTABLE STENT WITH COMPOSITE DESIGN

[75] Inventor: Eckhard Alt, Ottobrunn, Germany

[73] Assignee: Inflow Dynamics Inc., Arlington, Va.

[21] Appl. No.: 904,788

[22] Filed: Aug. 1, 1997

[51] Int. Cl.⁶ ................................................. A61F 2/06
[52] U.S. Cl. ................................ 623/1; 623/12; 606/195
[58] Field of Search .................................. 623/1, 11, 12; 606/192, 194, 195

[56] References Cited

U.S. PATENT DOCUMENTS

| 5,716,393 | 2/1998 | Lindenberg et al. | 623/1 |
| 5,749,919 | 5/1998 | Blanc | 623/12 |

Primary Examiner—Randy C. Shay

[57] ABSTRACT

A stent is adapted for deployment at a preselected site in a duct within the body of a patient to inhibit the lumen of the duct at that site from narrowing to a point that resists passage through the lumen. The stent is a generally cylindrical open-ended element having a perforated self-supporting sidewall of substantially uniform thickness adapted to be selectively expanded radially when the stent is to be deployed, to engage the wall of the duct and to resist radial contraction under forces exerted on said sidewall by the wall of the duct in the region of the engagement. The sidewall has greater rigidity in the midsection of the length of the cylindrical element and greater flexibility at each end thereof, by virtue of its having a composite design of different patterns, each pattern being a network of interconnected links with openings therebetween that determine the relative rigidity and flexibility of the sidewall along the length of the cylindrical element. The links may be sized to produce the differences in relative rigidity and flexibility along the length of the sidewall, and the sizing may undergo an abrupt or a continuous change between the midsection and each end of the cylindrical element. For sizing, the links may exhibit a decrease in width from the midsection to either end of the cylindrical element. Where the duct is a blood vessel with side branches emanating from the lumen of the main vessel, at least some of the openings between links in the midsection of the sidewall may be sized to enable access to the side branches from the lumen of the stent when the stent is deployed at the selected site in the main vessel.

15 Claims, 2 Drawing Sheets

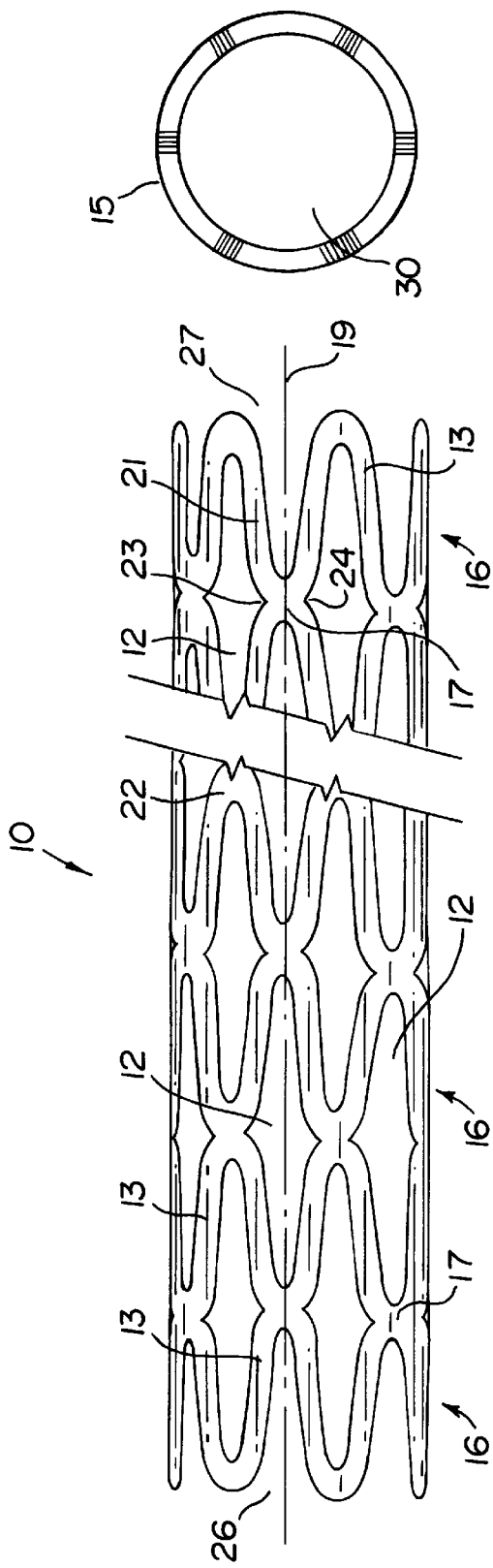
FIG. 1A (PRIOR ART)
FIG. 1B (PRIOR ART)
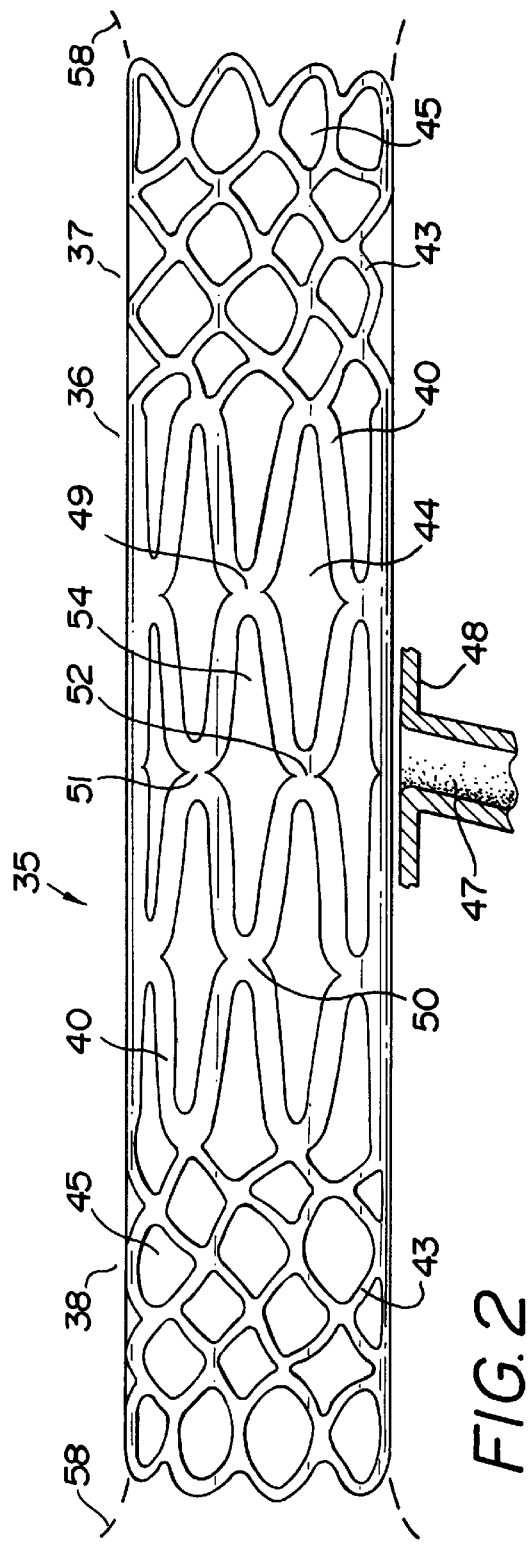
FIG. 2

FLEXIBLE IMPLANTABLE STENT WITH COMPOSITE DESIGN

BACKGROUND OF THE INVENTION

The present invention relates generally to stents which are implantable or deployable in a vessel or duct within the body of a patient to maintain the lumen of the duct or vessel open, and more particularly to improvements in stent structures, stenting procedures, and processes for making stents.

Stents are expandable vascular and endoluminal prostheses, usually employed to keep a particular site in the blood vessels open and unoccluded, especially in the coronary and femoral arteries, following treatment such as dilatation by balloon catheter angioplasty (i.e., percutaneous transluminal coronary angioplasty, or PTCA). But these devices are also quite useful in other applications as well, such as in other tracts or ducts in the human body where support of the tract or duct wall is required along a preselected target site to maintain the lumen open and unobstructed. Examples of such other applications are the tracheo-bronchial system, the biliary hepatic system, the esophageal bowel system, and the urinary tract system. A vascular stent in particular must be sufficiently dimensionally stable to keep the vessel and lumen open while resisting recoil of its elastic wall that naturally occurs when the site within the vessel or luminal structure has been subjected to outwardly directed forces that are necessary to expand the elastic fibers, compress fatty deposits on the wall, and/or to deploy the stent, and to prevent an acute closure following dissection of the vessel.

To date, various studies have demonstrated that coronary stenting has major clinical benefits. For example, among several recent studies, those designated as STRESS and BENESTENT have indicated that the implantation of coronary stents can serve not only to reduce acute complications following a balloon PTCA intervention in the coronary system, but also to improve the long term outcome. The local recoil of the vessel wall, which is normally a principal reason for restenosis after balloon PTCA, is prevented as a result of the scaffolding and support of the vessel wall provided by the stent. Experience gained from the profusion of coronary stenting has indicated that patients who had not been considered candidates for the procedure are now eligible for such implantation. In this respect, improvements in the design of stents and in the skill of the implanting physician have been factors in extending the suitability of stent implantation beyond merely type A or $B_1$ lesions (with reference to the American Heart Association (AHA)/American College of Cardiology (ACC) coronary stenosis morphology), to more severely curved, longer and complex lesions.

According to studies recently performed at the Technische Universtät München and the German Heart Center München, the mortality rate with stents in acute infarction decreases to less than 2%, which represents the lowest mortality reported to date with any kind of treatment for acute myocardial infarction. But the prerequisites for stenting continue to increase, especially for emergency interventions which are frequently encountered in contrast to elective procedures, making it imperative that stent design be improved to enable availability for use over a wider range of coronary morphology types.

Several different stent designs have become available for clinical use or experimental evaluation. Among these are the self-expanding mesh type, the coil type with a helical wire configuration typically of 100 to 200 micron ($\mu$) thickness, the slotted tube type such as that disclosed in co-pending U.S. patent application Ser. No. 08/599,880, filed Feb. 14, 1996, and its German counterpart application DE 19537872A1, and the multicellular type which is a modification of the slotted tube type with less surface coverage and smaller openings. Each of these stent designs has its individual benefits and limitations. Slotted tube stents provide the greatest support strength and the lowest recoil, which is particularly important for patients with very hard, even calcified, and a higher degree of stenosis. Recoil of less than 5% is experienced with slotted tube stents, whereas coil and multicellular stents typically allow recoil of about 10 to 15%. Consequently, within a short time after a stent of either of the latter types has been implanted in the vessel, the vessel diameter will decrease to some 10 to 15% of what it was when the balloon was fully inflated to deploy the stent.

While slotted tube stents allow the least recoil, they are somewhat less flexible than the other design types, and, to overcome this reduced flexibility, slotted tube stents of increased length generally incorporate a link or a bridge that interconnects two or more members of the basic principal design, such as shown in U.S. Pat. No. 5,449,323 of Pinchasik et al. Although such a design gives the longer stents—say 15 millimeters (mm), 23 mm, or even 30 mm versions—greater flexibility, it sacrifices mechanical strength at the site of the bridge. Coil stents tend to have wider openings and somewhat greater flexibility than the slotted tube stents, but exhibit less rigidity. Examples of various stent types are found in U.S. Pat. Nos. 5,443,498; 4,580,568; B1-4,733,665; 4,739,762; 5,102,417; and 5,195,984; European patents and applications EP 0221570B1; 0606165A1; and 0364787A1; and German patent DE 4334140A1.

It is a principal aim of the present invention to provide an improved stent of flexible but still mechanically supportive design, which is particularly suited for the longer configurations.

SUMMARY OF THE INVENTION

According to the invention, a composite stent is provided with a design or pattern of interconnected struts and openings between struts in its wall along the midsection of its length which is physically different from the design or pattern of interconnected struts and openings between struts at either end portion of the wall, so as to make the stent more rigid along its midsection to provide greater mechanical support than at either end portion, and more flexible at its end portions than along it midsection.

In use as a vascular stent to inhibit restenosis at a site along the wall of a coronary artery that exhibits stenosis, for example, the greater rigidity of the midsection allows the stent to squeeze all arteriosclerotic masses into the wall when deployed at the selected site, given that the narrowing of the vessel is most pronounced at the longitudinal center of the stenosis. Additionally, the more rigid midsection of the stent is better able to withstand recoil of the vessel wall in that region that occurs following deployment of the stent. The more flexible end portions of the stent allow the stent to more easily traverse tortuous paths that may be encountered during advancement or retraction of the stent through the lumen of the vessel, such as the aortic arch and the artery itself where the deployment site is in a coronary artery. Moreover, the end portions are made sufficiently long to create a smooth transition from the more rigid midsection of the stent to the native vessel, to better match the biomechanics of the native vessel by the artificial stent, and to flex with the repetitive movement of the blood vessel accompanying systole and diastole with beating of the heart.

The flexible end portions also attach intimal flaps or stabilize dissections which result from the initial expansion of the center stenosis. And the smooth transition from the stented region to the unstented vessel avoids a gradient of forces that would tend to provoke restenotic processes. End portion flexibility is also conducive to the development and use of longer stents because of the capability of advancement through tortuous vessels.

In an embodiment of a vascular or endoluminal stent adapted for deployment in a vessel or tract of a patient to maintain an open lumen therein, the stent is a hollow tube of biocompatible metal with distinctive end regions and a middle region between the end regions. Each of the middle and end regions has a multiplicity of openings through the open-ended wall of the tube, the openings being defined by surrounding struts in a network of interconnected struts constituting the tube wall. The struts in the middle region are wider than the struts in either end region so as to render the middle region relatively more rigid and the end regions relatively more flexible.

Preferably, the struts of each end region are substantially identical to the struts of the other end region. Also, the struts in the middle region have a more pronounced longitudinal orientation than the struts in either end region, so as to reduce friction that accompanies movement of the stent through the vessel or tract. Moreover, since at least part of the resistance and friction that would be encountered during advancement (or retraction) of the stent through the vessel is attributable to the presence of any transverse barriers relative to the direction of movement, it is important that the interconnection of the struts be such that there be no substantial protrusion thereof about the circumference of the tube, when the stent is either in its original state following manufacture, or in a slightly expanded or even compressed state when it is mounted on a balloon for advancement through the vessel to the target site. The stent of the present invention is configured in a way that assures a substantially symmetrical opening of the stent under the force of pressure exerted by the balloon during inflation thereof, as described more fully in the aforementioned co-pending '880 application.

Further, in at least one of the end regions, struts are shaped and interconnected in a way to compensate, by longitudinal extension, for a reduction in length of the stent upon expansion of the diameter of the stent during deployment at the preselected site in the vessel or tract. This feature tends to maintain the length of the stent substantially invariant in the undeployed and deployed states. Throughout the length of the stent, however, each of the struts has a rounded, preferably oval, cross-section, and the interconnecting points between the struts are notched to enhance symmetrical radial expansion of the stent during its deployment. The flexibility of the end portions is also aided by the provision of smaller openings in each end region than the openings in the middle region. At least some of the openings in the middle region are made sufficiently large to allow access to a vascular side branch of the vessel from the lumen of the stent.

The invention also encompasses a method of fabricating a stent to be deployed at a preselected site in a vessel or tract of a patient to maintain the lumen thereof open at the site. According to the method, an open-ended tube of predetermined length selected as a starting material is composed of a material constituting a self-supporting sidewall of substantially uniform thickness that defines an outer diameter of the tube smaller than the diameter of the lumen of the vessel or tract. Preferably, the selected material is a metal which is biocompatible with the tissue and blood of the body. Openings are formed in the sidewall to an extent that will allow the diameter of the tube lumen to be expanded to at least substantially the diameter of a fully open lumen of the vessel or tract at the site, without tearing the sidewall, while maintaining the self-supporting characteristic thereof, when the sidewall is subjected to a substantially uniform outwardly directed radial force of sufficient magnitude circumferentially along the entire length thereof. The pattern of the openings along the length of the tube is varied to render the sidewall more rigid along a substantial portion of its midsection than at either end thereof and more flexible at each end thereof than along that portion of midsection.

The step of forming openings in the sidewall is performed by cutting (e.g., perforating) the sidewall to provide a network of interconnected struts, in which the openings lie between the struts in the sidewall. Varying the pattern of the openings is performed by sizing the struts to provide relatively greater rigidity of the sidewall along the designated portion of midsection and relatively greater flexibility of the sidewall at each end thereof. Preferably, the sizing of the struts is performed to produce an abrupt change in the pattern of the openings at each end of the sidewall relative to the pattern of openings in the designated portion of the midsection. The sizing of the struts may be done to provide a linear decrease in the width of the struts at each end of the sidewall relative to the width of the struts in the designated portion of the midsection.

Where the stent is to be deployed in a main blood vessel having vascular side branches emanating from the main vessel, the sizing of struts in the designated portion of the midsection is performed to align at least some of the openings in the midsection with at least some of the vascular side branches to allow perfusion into the side branches from the main blood vessel when the stent is deployed at the site.

The varying of the pattern of the openings according to the method may also include shaping struts and interconnections therebetween in at least one circumferential segment of the length of the sidewall which is considerably less than its entire length, to produce a controlled lengthening of the circumferential segment sufficient to substantially compensate for reduction in length of the remainder of the tube when the diameter of the tube lumen is expanded to deploy the stent at the selected site. The pattern of the openings may further be varied by providing those struts in the designated portion of the midsection with a generally longitudinal orientation to reduce friction when the stent is being moved along the lumen of the vessel or tract to or from the preselected site.

BRIEF DESCRIPTION OF THE DRAWINGS

The above and still further aims, objects, features, aspects and attendant advantages of the present invention will become apparent from the following detailed description of a preferred embodiment and method of fabrication thereof constituting the best mode presently contemplated of practicing the invention, when taken in conjunction with the accompanying drawings, in which:

FIG. 1A is a side view of a vascular or endoluminal stent disclosed in the aforementioned co-pending '880 application, shown in a pre-opened state for use; and FIG. 1B is an end view of the stent of FIG. 1A;

FIG. 2 is a side view of a stent of composite design according to a preferred embodiment of the present invention;

DETAILED DESCRIPTION OF THE PRESENTLY-PREFERRED EMBODIMENT AND METHOD

Figure 3:
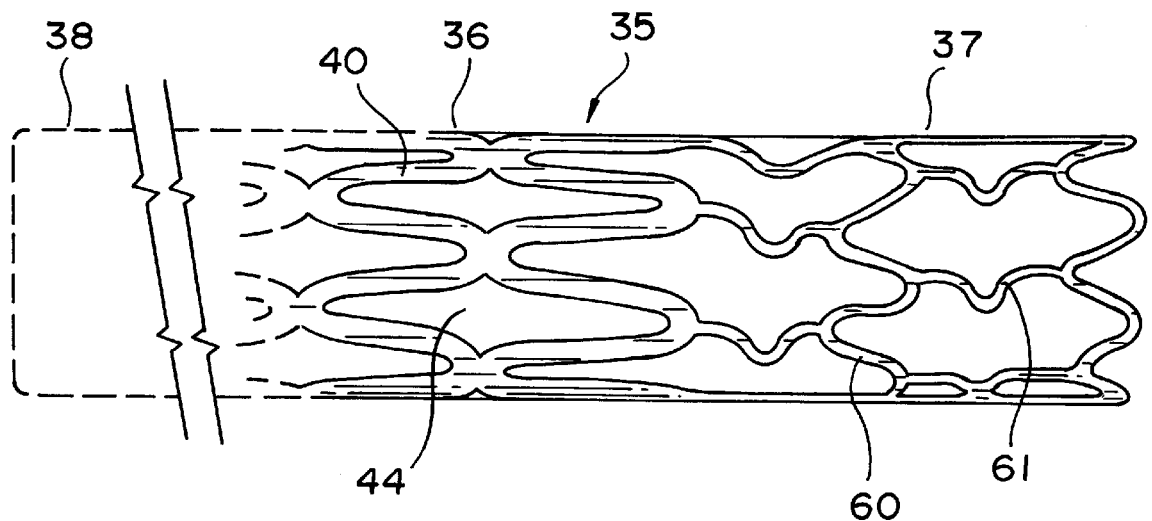
FIG. 3 is a fragmentary side view of a modified end region of the stent incorporating length-compensating means, which may replace one or both end regions in the stent embodiment of FIG. 2.

It should be noted with respect to the drawing that the Figures of drawings are not to scale. Where appropriate the representations are simplified, as by omitting details of the far side of the stent, which, although it would be viewable through the openings in the near side, would only clutter and obscure the details which are being described in the text; and by supplying full details of only a part of the stent pattern in some instances although it will be understood that the same pattern would be present throughout the enclosed dashed line in those instances. Also, a Figure or portion thereof may be exaggerated for emphasis.

A slotted tube stent design is disclosed in the aforementioned co-pending U.S. '880 patent application, and that design is a significant part of a presently preferred embodiment of the composite stent design of this invention. It should be observed, however, that the principles of the present invention apply equally well to other stent designs. As shown in FIG. 1A, the stent of the '880 application is in a "pre-opened" state as it would be supplied in volume for implantation by physicians at a medical center. Although described in a preferred embodiment as a vascular slotted tube stent, the stent may be used for other applications, in various ducts or tracts of the human body.

A biocompatible open-ended tube 10 has a wall 15 with a multiplicity of through-holes or openings 12 through it, defined and bounded by a plurality of serpentine elements 13, sometimes referred to herein as struts or links. The serpentine elements, which are cut out using a narrow laser beam, run circumferentially in juxtaposed sine wave-like patterns 16, each of the patterns resembling uniform multiple sinusoidal cycles. The removed material that formerly occupied openings 12 is discarded following the cutting. Adjacent patterns may be regarded as being offset from one another by a predetermined phase difference—here, 180°— at their points of interconnection 17 about the circumference of the tubular wall. Thus, in this example, adjacent patterns are connected crest to crest and trough to trough (crest and trough referring to the waveform shape). The sinusoidal patterns are uniformly displaced longitudinally along the axis 19 of the tube, i.e., the stent has a longitudinal regularly repeating serpentine pattern. Suitable materials for the tube include medical grade stainless, such as 316L stainless steel, tantalum, titanium, platinum, and iridium.

Each of the interconnecting points, such as 17 between serpentines 21 and 22, has a pair of confronting notches (e.g., 23 and 24) that serve to ease crimping of the stent onto the balloon, and to mandate symmetrical expansion of the stent when the mounting balloon of the balloon catheter (not shown) is inflated for deployment of the stent at the target site.

Openings 12 may be sized, for example, in a ratio of length to width ranging from 4:1 to 10:1, in a length in a range from 2.0 to 4.0 mm, and in a width in a range from 200 to 300 microns. Serpentine struts 13 may be dimensioned, for example, with a width in a range from 120 to 240 microns, and thickness in a range from 65 to 100 microns (i.e., the wall thickness). In the stent of the '880 application, each end 26, 27 of the tube 10 comprising the stent is a series of undulations in the serpentine element occupying that segment. The lumen 30 of the stent is shown in the end view of FIG. 1B.

Laser cuts are made in the wall of the tube to cleanly form the openings and serpentine elements, and to provide stent surfaces that are virtually burr- and protuberance-free. The laser cutting is programmed in a conventional manner, for precise definition of the stent pattern. Further processing of the product by electro-machining allows high current concentration for removal of sharp edges and corners in the tube structure. The overall result is a desirable rounding and smoothing of all sharp corners and edges which creates a rounded, preferably oval shaped cross-section of the serpentine ribs of metal remaining after such processing, that surround the openings. Elimination of sharp edges, corners, and burrs in the stent lessens the possibility of injury to the vessel wall during advancement and final deployment of the stent, and avoids damage to the membrane of the balloon on which the stent is crimped, advanced, and deployed. After this processing (and, of course, before the stent is mounted on a balloon), the patterned tube is annealed.

Longitudinal tapering of the stent wall thickness from its thickest portion at the longitudinal center of the tube to its thinnest portion at the ends serves to improve its flexibility at the ends and thereby enable the stent to be advanced more easily through the generally tortuous path of the human vascular system to the target site at which it is to be deployed. The tapering is performed on the outer diameter of the tube, by polishing in a smooth progression from its mid-section. This also provides greater compliance with the wall of the vessel at the implant site. The diameter of the tube's axial lumen remains uniform throughout the length of the tube, to preclude turbulence in the blood flow that might otherwise lead to thrombus formations. The present invention represents an improvement over this aspect of the invention disclosed in the '880 application, in the provision of a more rigid midsection of the stent and more flexible end regions.

Thus, unlike tube-type stents of the prior art, such as those of the Palmaz-Schatz type which use a system of parallel longitudinal struts and connecting bridges with rectangular openings in the tube wall, the stent of the '880 application has serpentines of a sinusoidal pattern running circumferentially which produces a rhombic, net-like structure. The serpentines have a periodic smooth interconnection in an integrated structure, with circumferential notches to facilitate both crimping and radial expansion, and rounded cross-sections. Most importantly, this design assures that, during its deployment on the inflating balloon, the stent will invariably undergo smooth and symmetric expansion.

In preparation for implantation, the stent is crimped onto a relaxed (deflated) expansion balloon, intermediate the ends of the balloon, which is affixed in a conventional manner at the distal end of a catheter body having an inflation lumen (not shown). The balloon is then inflated to a pressure of from about 0.2 to 0.4 atmospheres, sufficient to distend its end portions that extend beyond the respective ends of the stent without substantially expanding the crimped stent thereon.

The stent may be crimped onto the balloon by the implanting physician at the time the procedure is to be performed, or may be pre-mounted on the balloon and delivered as an assembly in a sterile package to be available to the implanting physician for the procedure. In a pre-mounting, the stent would be crimped on the slightly longer inflation balloon while the balloon is under vacuum, after which the balloon would be initially inflated to a pressure of from about 0.1 to about 0.5 (nominally, 0.2) atmospheres. The specific pressure selected is sufficient to partially inflate and distend the balloon at its distal and proximal ends that extend beyond the ends of the stent, but insufficient to expand the diameter of the mounted stent. The slight inflation at the ends of the balloon serves to firmly center the stent, protect the stent from being dislodged, and avoid scraping the leading edge of the stent against the vessel wall during advancement to the selected site. As will be described in greater detail below, the present invention in one of its aspects goes further to assure that the stent can traverse the path through the vessel without incident, even where the path is tortuous.

The stent as crimped on the balloon has a typical outer diameter in a range from about 0.9 to 1.2 mm. Typical diameter of the fully deployed stent may range from about 2.5 to 6.0 mm, sufficient for firm retention in the vessel at the selected site (e.g., the site of a stenosis in a coronary artery), and may even be partly imbedded in the vessel wall, to provide a smooth continuous lumen to the flow of blood.

Although stents generally are produced in lengths from about 5.0 to 25.0 mm, two "standard" lengths have been typically provided in the art prior to the stent described in the '880 application, one standard length being fixed in a range from about 8.0 to 9.5 mm, and the other about 15.0 mm, fuse with the customary implantation balloon lengths of 10 mm and 20 mm. Other stent lengths have been made available on a custom basis, but it may be necessary to implant two stents end to end when the length of the lesion at the target site is greater than that accommodated by a single stent.

After the stent has been advanced on the balloon catheter to the target site in the vessel, it is deployed by steadily increasing the inflation pressure of the balloon so as to expand the diameter (and thereby, the lumen opening) of the stent to a size appropriate for the vessel diameter. As the stent diameter increases, the stent length decreases, although ordinarily these two inter-related dimensional changes would not occur in a 1:1 ratio. Rather, the reduction in length normally occurs at a much smaller rate, but must be factored into the calculation to determine in advance whether use of a single stent will afford sufficient coverage of the lesion at he target site.

In the stent of the '880 application, special elements incorporated into the stent are designed to undergo a change that leads to a predetermined increase in length of the stent as it is expanded in diameter, to counteract and compensate what would otherwise be a reduction in length attributable to that expansion. To that end, a circumferential segment of the stent interrupts the regularity of the above-described stent design by introducing transversely oriented serpentine elements (not shown) that run longitudinally within the tube wall in juxtaposed at least partial sine wave-like patterns. Like the major pattern described above, the transverse patterns are cut into the wall with a narrow beam laser, operating on a programmed cutting cycle. Although such a succession of two different stent designs longitudinally along the stent wall constitutes a composite stent design, unlike the composite stent design of the present invention the compensating serpentine elements of the '880 application are constructed and adapted solely to maintain the length of the tube substantially invariant with radial expansion of the stent. There is no corresponding change in stent design itself to achieve a more rigid middle region or more flexible end regions.

The transverse serpentines used for automatic compensation of length during radial expansion of the stent of the '880 application run longitudinally, are connected to selected points of the most closely adjacent circumferential serpentines, and are separated from one another at predetermined regions about the circumference of the tube. The separations are provided to avoid the imposition of constraints on the diameter of the stent at the location of the transverse elements during expansion of the stent, and in the stent of the '880 application, do not substantially affect the rigidity of the stent.

Automatic maintenance of the length of the stent during its deployment eliminates a need for the physician to calculate changes in length of the stent to assess adequacy of coverage of the affected tissue at the target site in the vessel. Also, the length-compensation feature can avoid a need to implant two stents end-to-end to accommodate the length of the lesion at the target site, where the length saved by the automatic maintenance allows a single standard-sized stent to fit.

An embodiment of a stent in accordance with the present invention is illustrated in FIG. 2. The stent 35 is a composite of two (or more, if desired) different designs, for the primary purpose of providing the greatest rigidity—and therefore, greater support of the vessel wall—in the central or middle region 36 of the stent length; and the greatest flexibility—and therefore, greater ease of movement along the tortuous path of the vessel—in the end regions 37, 38 of the stent. Thus, the composite stent advantageously uses one design or configuration in its middle region and a second configuration in each of its end regions.

The middle region 36 of the composite stent is configured preferably with the same slotted tube stent design as that described in the '880 application, summarized above. In this region, the individual struts 40 cut in patterns in the wall of tube 41 are relatively wide—e.g., 180 micrometers ($\mu$m, or simply microns ($\mu$))—compared to the considerably narrower individual struts 43 (e.g., 80 to 100$\mu$) in the multicellular design of the end regions 37 and 38. Additionally, the shape of the struts 40 in the middle region is serpentine, the sinusoidal type of pattern running circumferentially and thus giving the struts a pronounced longitudinal orientation in that region. This is to be contrasted with the smaller, more circular shape of the struts 43 in the end regions of the composite stent which assist, along with the narrower strut width, in providing greater flexibility of the end regions. Although the change in stent design from the midsection to the end regions is shown in the Figures as being abrupt, it will be understood that a continuous or substantially continuous change or variation in the design may be employed without departing from the principles of the invention.

The longer struts (including interconnected struts) in the middle region also mandate that this region has larger openings 44 than the openings 45 in the end regions. These larger openings allow better access to vascular side branches such as 47, emanating from the main blood vessel 48 in which the stent is deployed. By way of example, the longitudinal distance between pattern interconnection points 49 and 50 is approximately 3.33 mm when the stent is in a normal closed condition (i.e., in its original, uncrimped and unexpanded state). When the stent is opened to its fully expanded, deployed state, this distance may decrease to about 3.0 mm. At the same time, the transverse distance between pattern interconnection points 51 and 52 may increase from about 1.0 mm to about 1.6 mm. Now assume that an opening 54 bounded by those points is aligned with a side branch such as 47. The side branch may have a lumen diameter of about 2.0 mm, and by virtue of the size of opening 54, the stent will not substantially impede perfusion from the lumen of the main blood vessel to the side branch. Additionally, opening 54 will allow access from the lumen of the stent into the lumen of the side branch, and the exemplary dimensions set forth above would be sufficient to even thread and advance a second stent mounted on a balloon (of a separate balloon catheter (not shown)) having an outer diameter of 1.0 mm into the side branch for stenting at another site in that branch.

As a result of the configuration of multicellular design and narrower struts at the end regions, and slotted design, wider struts in the middle region, both the distal end 38 and the proximal end 37 of the stent are more flexible than the midsection 36. Thus, the stent is more easily advanced (or withdrawn) through a winding or tortuous path of the vessel, with consequent less likelihood of injury to the vessel as the stent traverses therethrough. Even the presence of a slightly inflated end of the mounting balloon (indicated in an exaggerated manner by the dashed lines 58), which results from a slight inflation of the balloon after the stent is crimped thereon, does not provide the same degree of advantage in this respect, nor lessen the significance of this flexibility. It will be observed, also, that this flexibility is achieved without narrowing the thickness of the wall at either end of the stent.

An advantage is achieved as well from the longitudinal orientation of the midsection struts, in that this orientation substantially reduces the friction that would otherwise be created by the advancing stent. The rounding and notching of the serpentine elements is carried into the multicellular design pattern of the end regions 37 and 38 to assure that a substantially symmetrical opening of the overall stent is achieved as the mounting balloon is inflated during partial expansion at the outset and further expansion at final stent deployment. Consequently, no protuberances are encountered in the stent configuration to interrupt its relatively smooth cylindrical outer surface presented to the vessel wall either during movement through the vessel, which further alleviates friction, or at the target site, which alleviates trauma. These results are achieved despite the greater rigidity of the middle region compared to the end region. The greater width and length of the midsection struts offers considerably greater mechanical support than the end region struts, and this greater support is provided in the stent of the present invention precisely where a stenosis in a vessel exhibits the greatest degree of narrowing—at the center of the lesion.

In the fragmentary side view of another embodiment of the invention shown in FIG. 3, stent 35 again has a middle region or midsection 36 comprising the slotted stent design of the '880 application. Here, however, the end regions (only the proximal one 37 of which is shown) comprise a stent design or pattern that provides means for compensating for a shortening of the length of the stent when it is deployed. Additionally, this end region design provides a flexibility of the structure approaching that of the end region of the embodiment of FIG. 2. The width of the struts 40 in the middle region is considerably greater than the width of struts 60 in the end region, as in the previous embodiment. The most significant functional difference from the FIG. 2 embodiment is that the struts 60, 61 in the end region are shaped and interconnected to lengthen the end region to compensate for the shortening of the length elsewhere in the stent when the stent is deployed.

During the radial expansion of the stent's lumen, struts 61 are stretched and straightened by the forces that are tending to expand the serpentines in which struts 40 of the midsection and struts 60 of the end region are disposed. This action causes a lengthening of the cylindrical segment of the stent constituting the end region 37 which substantially counteracts—by compensating for—the shortening of stent length attributable to radial expansion in the middle region as well as to any contribution of similarly oriented struts (e.g., 60) in either or both end regions.

It should be observed that the length-compensating means need not occupy both end regions, or even an entire single end region, but may be limited to a smaller circumferential segment of that region. In that respect, the composite stent of the present invention may have one end region—preferably the distal end—of multicellular design such as illustrated in both end regions of FIG. 2, and the other end region that provides both the flexibility and the length-compensating design of the end region illustrated in FIG. 3.

Figure 4:
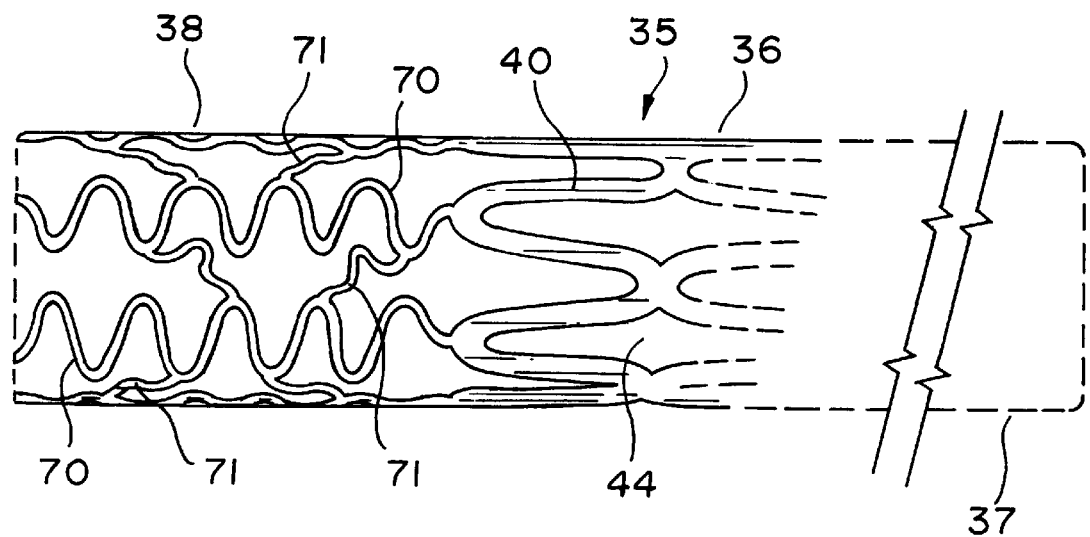
FIG. 4 is a fragmentary side view of another alternative embodiment of a length-compensating means for use as the end region.

FIG. 4 is a side view of a portion of yet another alternative embodiment of an end region of the stent of the present invention. In this embodiment, end region 38 of stent 35 has struts 70 which are serpentine and run with a longitudinally oriented sinusoidal pattern relative to the axis of the stent. These struts are connected at the end adjacent the middle region 36 to the respective crest of the confronting struts 40 of the middle region. However, the sinusoidal patterns containing struts 70 are separated circumferentially from one another. Except at predetermined points where a sinusoidal pattern is interconnected to the adjacent sinusoidal pattern by a diagonally extending serpentine 71. The latter runs from the crest (or trough) of a wave in one strut 70 pattern to the trough (or crest) of the wave in the next adjacent strut 70 pattern.

With this design configuration, when the stent is deployed the diameter of its lumen is expanded, which causes the diagonal struts 71 to be stretched circumferentially. The longitudinal struts 70, however, are stretched transversely to some extent by the stretching of the diagonal struts, but are also stretched longitudinally to effect a lengthening of the stent in compensation for the shortening of the stent elsewhere.

With respect to the relative lengths of the different regions of the composite stent, by way of example and not of limitation, a 15 mm long stent may have a midsection 36 of 7 mm length, and end regions 37 and 38 of 4 mm length each. Such relative lengths of end regions to middle region provide a smooth transition at each end of the stent between the native vessel itself and the more rigid characteristic of the midsection, and to better match the biomechanics of the native vessel by the artificial stent, with all of the benefits thereof which have been described. In each embodiment of the stent, the struts are sized to provide a predetermined decrease in strut width from the midsection of the stent to each end region of the stent.

Other aspects disclosed in the '880 application, such as balloon mounting of the stent, and implantation and deployment of the stent in the vessel, apply equally to the present invention. Hence, the entirety of the '880 application is incorporated herein by reference.

Although a preferred embodiment and method of the invention have been shown and described as indicative of the best mode presently contemplated of practicing the invention, it will be apparent to those skilled in the art from a consideration of the foregoing detailed description that variations and modifications of the described embodiment and method may be made without departing from the true spirit and scope of the invention. It is therefore intended that the invention shall be limited only by the following claims and the rules and principles of applicable law.

What is claimed is:

1. A vascular or endoluminal stent adapted for deployment in a vessel or tract of a patient to maintain an open lumen therein, comprising a biocompatible hollow tube with distinctive end regions and a middle region between the end regions, each of said middle and end regions having a multiplicity of openings through an open-ended wall of the tube, said openings being defined by surrounding struts in a network of interconnected struts, the struts in the middle region being wider than the struts in either end region, whereby to render the middle region relatively more rigid and the end regions relatively more flexible.

2. The stent of claim 1, wherein the struts of each end region are substantially identical to the struts of the other end region.

3. The stent of claim 1, wherein the struts in the middle region have a pronounced longitudinal orientation, whereby to reduce the friction between the middle region and the vessel or tract through which the stent moves during advancement of the stent therethrough to a predetermined site at which the lumen is to be maintained open.

4. The stent of claim 1, wherein at least one of the end regions includes means to compensate for a reduction in length of the stent upon expansion of the diameter of the stent during deployment thereof at a predetermined site in the vessel or tract at which the lumen is to be maintained open, whereby to maintain the length of the stent substantially invariant between an undeployed state and a deployed state.

5. The stent of claim 1, wherein each of said struts has a rounded cross-section.

6. The stent of claim 1, wherein interconnecting points between the struts are notched to enhance symmetrical radial expansion of the stent during deployment thereof.

7. The stent of claim 1, wherein said openings in each end region are smaller than the openings in the middle region.

8. The stent of claim 7, wherein at least some of the openings in the middle region are sufficiently large to accommodate perfusion of blood and access for a smaller diameter stent therethrough to a side branch of the vessel or tract from the lumen of the stent.

9. A stent adapted for deployment at a preselected site in a duct within the body of a patient to inhibit the lumen of the duct at said site from narrowing to a point that resists passage therethrough, said stent comprising a generally cylindrical open-ended element having a permeable self-supporting sidewall of substantially uniform thickness adapted to be selectively expanded radially when the stent is to be deployed, to engage the wall of the duct and to resist radial contraction under forces exerted on said sidewall by the wall of the duct in the region of engagement therebetween, said sidewall being more rigid in the midsection of the length of said cylindrical element and more flexible at each end thereof, said sidewall comprising a network of interconnected links with openings therebetween determining the relative rigidity and flexibility of the sidewall along the length of said cylindrical element.

10. The stent of claim 9, wherein said links are sized to produce predetermined differences in relative rigidity and flexibility of the sidewall along the length of said cylindrical element.

11. The stent of claim 10, wherein the links undergo a decrease in width from said midsection to either end of said cylindrical element to provide the sizing that produces said predetermined differences.

12. The stent of claim 9, wherein the links with openings therebetween undergo an abrupt change between said midsection and each end of said cylindrical element, the abrupt change affecting the relative rigidity and flexibility of the sidewall at either side of said change.

13. The stent of claim 9, wherein the duct is a main duct with branches therealong to side ducts emanating from the lumen thereof, and wherein at least some of the openings between links in said midsection are sized for access to side ducts from the lumen of said main duct.

14. The stent of claim 9, wherein the links include means for counteracting any substantial change in the length of said cylindrical element during radial expansion of the sidewall for deployment of the stent.

15. The stent of claim 9, wherein said cylindrical element comprises a medical grade stainless steel.

* * * * *